(12) United States Patent
Kim et al.

(10) Patent No.: US 9,962,384 B1
(45) Date of Patent: May 8, 2018

(54) LEVOSIMENDAN COMPOUND FOR PREVENTING OR TREATING TAU-RELATED DISEASES

(71) Applicant: KOREA INSTITUTE OF SCIENCE AND TECHNOLOGY, Seoul (KR)

(72) Inventors: Yun Kyung Kim, Seoul (KR); Sung Su Lim, Seoul (KR); Do Hee Kim, Seoul (KR); Md. Mamunul Haque, Seoul (KR); Seul Gi Shin, Seoul (KR); Ha Eun Lee, Seoul (KR); Tae Hun Kim, Seoul (KR); Sang Min Lim, Seoul (KR); Ae Nim Pae, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days. days.

(21) Appl. No.: 15/697,728

(22) Filed: Sep. 7, 2017

(51) Int. Cl.
    *A61K 31/50* (2006.01)
    *A61K 47/36* (2006.01)
    *C07D 237/10* (2006.01)

(52) U.S. Cl.
    CPC .............. *A61K 31/50* (2013.01); *A61K 47/36* (2013.01); *C07D 237/10* (2013.01)

(58) Field of Classification Search
    None
    See application file for complete search history.

(56) References Cited

U.S. PATENT DOCUMENTS 8,809,302 B2 * 8/2014 Cohen .................. A61K 31/137
                                                    514/171

FOREIGN PATENT DOCUMENTS

EP        0565546 B1 *  3/1995  .......... C07D 237/04

OTHER PUBLICATIONS

Tania F. Gendron et al., "The role of tau in neurodegeneration", Molecular Neurodegeneration, Mar. 2009, pp. 1-19, vol. 4, No. 13.
Itsushi Minoura et al., "Dielectric Measurement of Individual Microtubules Using the Electroorientation Method", Biophysical Journal, May 2006, pp. 3739-3748, vol. 90.
Marco D. Mukrasch et al., "Sites of Tau Important for Aggregation Populate β-Structure and Bind to Microtubules and Polyanions", The Journal of Biological Chemistry, 2005, pp. 24978-24986, vol. 280, No. 26.
Gerard Drewes et al., "Microtubule-associated Protein/Microtubule Affinity-regulating Kinase (p110$^{mark}$)", The Journal of Biological Chemistry, 1995, pp. 7679-7688, vol. 270, No. 13.
J. Biernat et al., "Phosphorylation of Ser$^{262}$ Strongly Reduces Binding of Tau to Microtubules: Distinction between PHF-like Immunoreactivity and Microtubule Binding", Neuron, Jul. 1993, pp. 153-163, vol. 11.
In-Cheol Choi, "New Inotropic Agent-Levosimendan", Korean J. Anesthesiol, Nov. 2006, pp. 519-527, vol. 51 No. 5.

* cited by examiner

*Primary Examiner* — Brian J Davis
(74) *Attorney, Agent, or Firm* — Rabin & Berdo, P.C.

(57) ABSTRACT

Disclosed is a levosimendan compound, an optically active isomer thereof, or a pharmaceutically acceptable salt thereof, which is used for the prevention and/or treatment of diseases caused by tau aggregation or phosphorylation, such as neurodegenerative diseases (e.g., Alzheimer disease). In accordance with yet another aspect of the present invention, there is provided a health functional food for preventing or treating tau aggregation-related diseases, containing a levosimendan compound or a pharmaceutically acceptable salt, stereoisomer or solvate thereof.

3 Claims, 8 Drawing Sheets

LEVOSIMENDAN COMPOUND FOR PREVENTING OR TREATING TAU-RELATED DISEASES

BACKGROUND OF THE INVENTION

Field of the Invention

The present invention relates to a levosimendan compound, an optically active isomer thereof, or a pharmaceutically acceptable salt thereof, which is used for the prevention and/or treatment of diseases caused by tau aggregation or phosphorylation.

Description of the Prior Art

Tau is a microtubule-associated protein (MAP) having a molecular weight of 50,000 to 70,000, which is primarily expressed in neuronal axons, functions to stabilize microtubules (MTs), and shows molecular diversity by its phosphorylation.

In the human brain, six tau isoforms are generated by insertion of 29 or 58 amino acid residues in the N-terminal region and mRNA alternative splicing of 3 or 4 repeating structures (also referred to as microtubule-associated sites).

In a healthy neuron, tau stabilizes microtubules by promoting axonal outgrowth and neuronal cell polarization. When pathologically hyperphosphorylated, tau dissociates from microtubules and aggregated (Gendron T F, Petrucelli L (2009) The role of tau in neurodegeneration. Mol. Neurodegener. 4: 13). A structural framework for tau aggregation has been suggested. Evidences have been suggested that insoluble filaments are formed from 10 soluble monomers, and such filaments associate into higher order structures, called neurofibrillary tangles (NFTs). Full-length human tau contains a microtubule-binding domain consisting of four conserved sequence repeats. Positively charged residues in the sequence repeats are important for binding with the highly negatively charged microtubules (20 to 30 electrons per αβ-tubulin dimer) (Minoura I, Muto E (2006) Dielectric measurement of individual microtubules using the 5 electroorientation method. Biophys. J. 90: 3739-3748; Mukrasch M D, Biernat J, von Bergen M, Griesinger C, Mandelkow E, et al. (2005) Sites of tau important for aggregation populate beta-structure and bind to microtubules and polyanions. J. Biol. Chem. 280: 24978-24986). Tau's binding affinity for microtubules is also actively controlled by phosphorylation, which drives dynamic rearrangement of the microtubule network. Abnormal tau hyperphosphorylation disrupts the balance and dramatically reduces its affinity for microtubules (Drewes G, Trinczek B, Illenberger S, Biernat J, Schmitt-Ulms G, et al. (1995) Microtubule-associated protein/microtubule affinity-regulating kinase (p110mark). A novel protein kinase that regulates taumicrotubule interactions and dynamic instability by phosphorylation at the Alzheimer-specific site serine 262. J. Biol. Chem. 270: 7679-7688; Biernat J, Gustke N, Drewes G, Mandelkow E M, Mandelkow E (1993) Phosphorylation of Ser262 strongly reduces binding of tau to microtubules: distinction between PHF-like immunoreactivity and microtubule binding. Neuron 11: 153-163).

Tauopathy is a group of neurodegenerative diseases caused by the abnormal accumulation of tau proteins in neurons due to tau hyperphosphorylation and aggregation, and is a hallmark of various neurodegenerative diseases. Tau protein aggregates that appear in tauopathy patients are mainly found in neuronal cell bodies and dendrite, called neurofibrillary tangles (NFT) and neuropil threads. Neurofibrillary tangles are composed of paired helical filaments (PHFs) of aggregated and hyperphosphorylated tau protein, unlike normal tau protein. Although the role of abnormal tau protein aggregation, which appears in tauopathy, in a severe disease stage, has not been clearly known, it is similar to an aggregation phenomenon that appears commonly in neurodegenerative brain diseases.

Typical tau-related diseases include Alzheimer disease, Parkinson's disease, tauopathy, vascular dementia, acute stroke, traumatic injury, cerebrovascular disease, brain cord injuries, spinal cord trauma, peripheral neuropathy, retinopathy, glaucoma, progressive supranuclear palsy, corticobasal degeneration, argyrophilic grain disease, peak disease, and inherited frontotemporal dementia. Despite active researches in the relevant field, specific mechanisms of signaling and toxicity expression in tau protein-mediated diseases have not been clearly found. In addition, a distinct therapeutic method or agent against tau-related diseases has not yet been reported.

Accordingly, the present inventors have conducted studies on tau aggregation and phosphorylation to identify a new tau inhibitor, and as a result, have found that levosimendan reduces tau aggregation and phosphorylation, thereby completing the present invention.

SUMMARY OF THE INVENTION

Whether or not a levosimendan compound is useful for the prevention and/or treatment of diseases caused by tau aggregation or aggregation has not been known.

Accordingly, it is an object of the present invention to a levosimendan compound or a pharmaceutically acceptable salt, stereoisomer or solvate thereof, or a composition containing the same, for use in a method for preventing or treating tau-related diseases.

In accordance with one aspect of the present invention, there is provided a levosimendan compound or a pharmaceutically acceptable salt, stereoisomer or solvate thereof, for use in a method for preventing or treating tauopathy or its symptoms.

The levosimendan compound may be represented by the following formula 1:

Formula 1

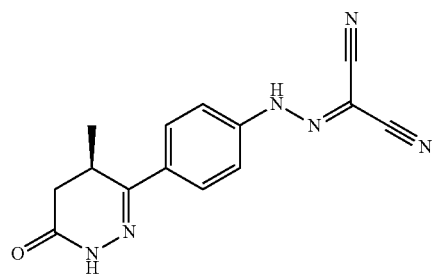 [SMILES: C[C@@H]1CC(=O)NN=C1c1ccc(NN=C(C#N)C#N)cc1]

The levosimendan compound preferably inhibits tau aggregation or phosphorylation, and more preferably does not influence changes in tau kinase activity.

The levosimendan compound may prevent additional aggregation of aggregated tau and dissociate aggregated tau.

In accordance with another aspect of the present invention, there is provided a composition for preventing or treating tau aggregation-related diseases, containing: a levosimendan compound or a pharmaceutically acceptable salt, stereoisomer or solvate thereof; and at least one pharmaceutically acceptable carrier.

The composition may further contain an active agent selected from the group consisting of an antioxidant, a cholinesterase inhibitor, and a combination thereof.

The tau aggregation-related diseases may be selected from the group consisting of Alzheimer disease, Parkinson's disease, tauopathy, vascular dementia, acute stroke, traumatic injury, cerebrovascular disease, brain cord injuries, spinal cord trauma, peripheral neuropathy, retinopathy, and glaucoma. In addition, the tauopathy is preferably selected from the group consisting of progressive supranuclear palsy, corticobasal degeneration, argyrophilic grain disease, peak disease, and inherited frontotemporal dementia.

In accordance with still another aspect of the present invention, there is provided a method for inhibiting tau aggregation, comprising treatment with a levosimendan compound or its derivative.

The method for inhibiting tau aggregation may comprise treating a cell line with a levosimendan compound or its derivative in vitro.

The method for inhibiting tau aggregation may be for inhibition of tau hyperphosphorylation.

In accordance with yet another aspect of the present invention, there is provided a health functional food for preventing or treating tau aggregation-related diseases, containing a levosimendan compound or a pharmaceutically acceptable salt, stereoisomer or solvate thereof.

DETAILED DESCRIPTION OF THE INVENTION

Unless otherwise defined, all technical terms used in the present invention have the same meanings as understood by those skilled in the art. In addition, although a preferred method or sample is described in the specification, those similar or equivalent thereto fall within the scope of the present invention.

The present invention is directed to a levosimendan compound or a pharmaceutically acceptable salt, stereoisomer, solvate or derivative thereof, for use in a method for preventing or treating tauopathy or its symptoms.

Levosimendan is known as a calcium sensitizer drug that is used for treatment of congestive heart failure. This drug binds to cardiac troponin C to increase $Ca^{2+}$ myofilament responsiveness to thereby increase muscle contraction. In addition, it acts as a vasodilator that opens the KATP channel of cardiomyocytes to thereby exhibit an anti-ischemic effect and an antistunning effect (In-Cheol Choi (2006), New Constriction Promoter-Levosimendan. Korean J Anesthesiol 51: 519-27).

However, whether or not the levosimendan compound is useful for the prevention and/or treatment of diseases caused by tau aggregation or phosphorylation has not yet been clearly known. Drug repositioning refers to an attempt to review existing drugs and pharmaceuticals in order to apply them for new indications (diseases). Drug repositioning can reduce the time and cost required for drug development and shows low failure rate in drug toxicity studies and clinical studies, and thus it is used as a new drug development strategy. As part of drug repositioning, the present invention is characterized in that the levosimendan compound is applied against tau aggregation or phosphorylation.

Until now, an agent and a mechanism, which may affect tau aggregation and phosphorylation, have not been clearly established. Therapeutic agents which are currently being studied include a CDK5 (cyclin-dependent kinase 5) inhibitor, propentofylline (PPE), N-phenylamines, quinoxalines, methylene blue, and the like. Among them, methylene blue is known to be effective in inhibiting tau protein aggregation. The methylene blue was used as a positive control in the Examples below, and was shown to have cytotoxicity higher than that of the levosimendan compound according to the present invention (see FIG. 2).

The levosimendan compound may be represented by the following formula 1:

Formula 1

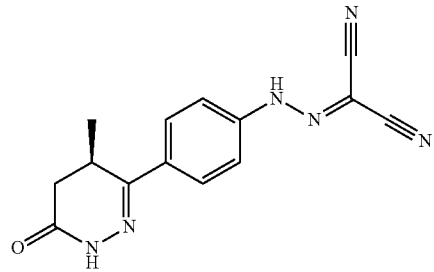 [SMILES: C[C@@H]1CC(=O)NN=C1c1ccc(NN=C(C#N)C#N)cc1]

The term "levosimendan compound" is meant to include all the compound itself and its pharmaceutically acceptable salt, hydrate, solvate, isomer and prodrug.

The levosimendan compound inhibits tau aggregation and phosphorylation, and does not affect changes in tau kinase activity. Furthermore, the levosimendan compound prevents additional aggregation of aggregated tau, and dissociates the aggregated tau.

Figure 3:
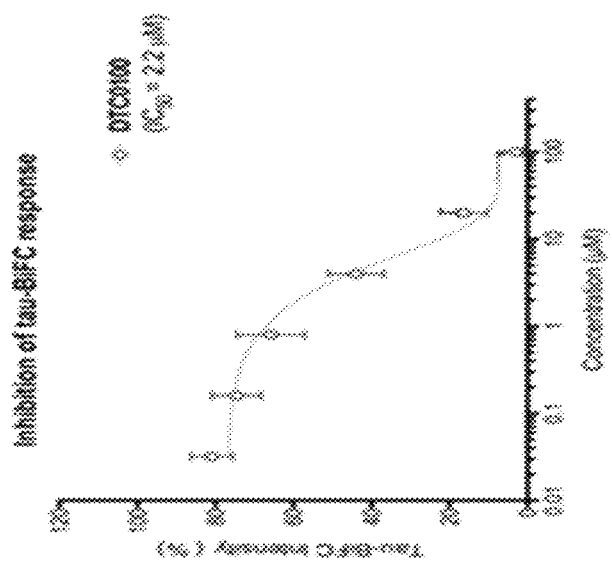
FIG. 3 shows the results of measuring the concentration-dependent intracellular tau aggregation inhibitory activity of a levosimendan compound in an example of the present invention.
Figure 3:
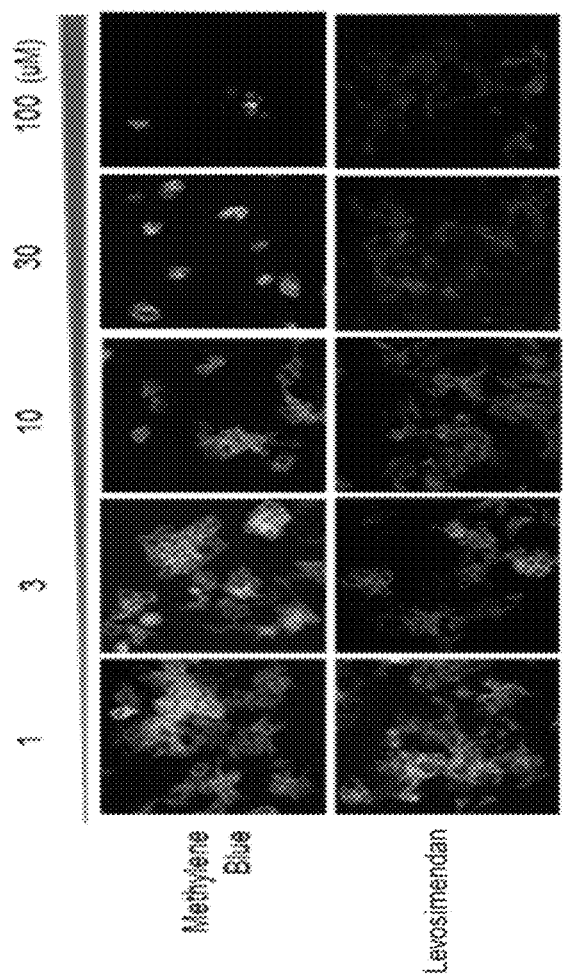
Figure 4:
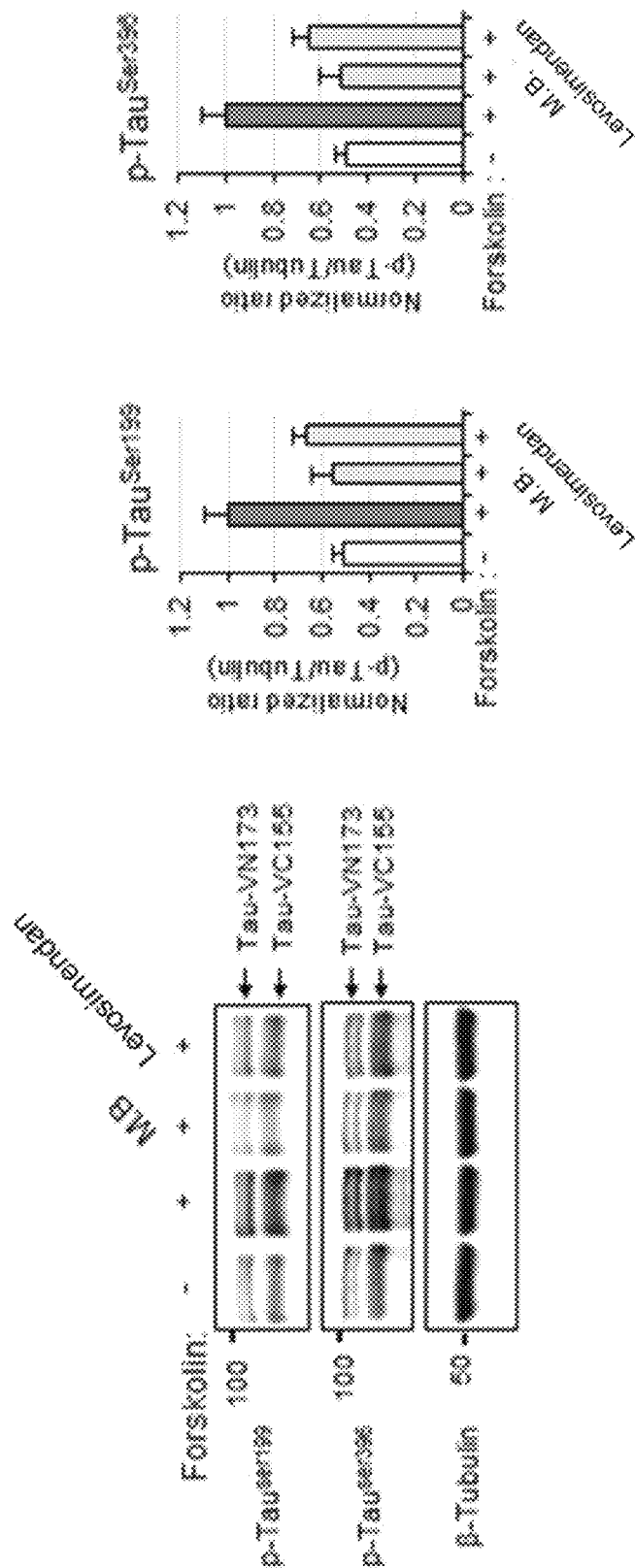
FIG. 4 shows the results of measuring the tau phosphorylation-reducing activity of a levosimendan compound in an example of the present invention.

When a cell line treated with a compound (forskolin) inducing tau aggregation was treated with the levosimendan compound, the tau aggregation inhibitory effect of the levosimendan compound was observed (see FIG. 3), and the tau phosphorylation-reducing effect of the levosimendan compound was also observed (see FIG. 4).

The present invention is also directed to a composition for preventing or treating tau aggregation-related diseases, the composition containing: a levosimendan compound or a pharmaceutically acceptable salt, stereoisomer or solvate thereof; and at least one pharmaceutically acceptable carrier.

The composition of the present invention may be prepared to contain at least one pharmaceutically acceptable carrier in addition to the levosimendan compound as an active ingredient. The pharmaceutically acceptable carrier that is used in the present invention may be a diluent, a lubricant, a binder, a disintegrant, a sweetener, a dispersing agent, a surfactant, a preservative, saline, sterile water, Ringer's solution, buffered saline, dextrose solution, maltodextrin solution, glycerol, ethanol, liposome, and a mixture of two or more thereof. If necessary, the composition may contain other conventional additives, including antioxidants, buffer, bacteriostatic agents, fragrances, vitamins and the like. In addition, the composition may be formulated as liquids, suspensions, powders, granules, pills, capsules or tablets, and a target organ-specific antibody or other ligands may be coupled to the carrier before use so that the levosimendan compound can act specifically in the target organ.

The composition according to the present invention may further contain an active agent selected from the group consisting of an antioxidant, a cholinesterase inhibitor, and a combination thereof. The antioxidant that is used in the present invention may be one or more selected from the group consisting of α-tocopherol, vitamin C (ascorbic acid), vitamin C palmitate, butylhydroxyanisole, dibutylhydroxytoluene, citric acid, erythorbic acid, fumaric acid, maleic acid, maltodextrin, potassium metabisulfide, sodium metabisulfide, propionic acid, propyl gallate, sodium ascorbate, sodium sulfate, tymol, cyclodextrin, and sulfobutylether β-cyclodextrin.

The cholinesterase inhibitor is a substance that inhibits the activity of cholinesterase and inhibits the hydrolysis of acetylcholine in vivo, and is also involved in activation of cholinergic nerves (parasympathetic nerve and motor nerves). The cholinesterase inhibitor that is used in the present invention may be one or more selected from the group consisting of donepezil, rivastigmin, galantamine, butylcholinesterase, phenserine, huperzin A and the like.

The compound according to the present invention has tau aggregation inhibitory activity, and is useful as an active ingredient of a medicament for the prevention and/or treatment of diseases selected from the group consisting of Alzheimer disease, Parkinson's disease, tauopathy, vascular dementia, acute stroke, traumatic injury, cerebrovascular disease, brain cord injuries, spinal cord trauma, peripheral neuropathy, retinopathy, and glaucoma. The tauopathy may be selected from the group consisting of progressive supranuclear palsy, corticobasal degeneration, argyrophilic grain disease, peak disease, and inherited frontotemporal dementia.

The present invention is also directed to a method for inhibiting tau aggregation, comprising treatment with a levosimendan compound or its derivative.

For example, tau hyperphosphorylation may be inhibited by treating a cell line with a levosimendan compound in vitro.

The present inventors have first found that in vitro treatment of a cell line with the levosimendan compound can inhibit tau hyperphosphorylation in the cell line.

The present invention is also directed to a health functional food for preventing or treating tau aggregation-related diseases, containing a levosimendan compound or a pharmaceutically acceptable salt, stereoisomer or solvate thereof.

The health functional food may be formulated as a conventional health functional food formulation known in the art. For example, the health functional food may be prepared in the form of various foods, beverages, gums, teas, vitamin complexes, health supplement foods, powders, granules, tablets, capsules, suspensions, emulsions, syrups, jellies, or drinks. The health functional food may further contain materials and components that are generally added in food preparation. For example, the health functional food may contain disaccharide, polysaccharide, dextrin, cyclodextrin, various nutrients, vitamins, electrolytes, flavoring agents, colorants and flavor enhancers, pectic acid and its salt, alginic acid and its salt, organic acid, a protective colloidal thickener, a pH adjusting agent, a stabilizer, a preservative, glycerin, a carbonating agent, and the like.

Hereinafter, the present invention will be described in further detail with reference to examples. However, it will be obvious to a person skilled in the art that these examples are for illustrative purposes only and are not intended to limit the scope of the present invention.

Furthermore, the following examples were performed based on tau-BiFC cell model. The tau-BiFC cell model is a reliable system for monitoring the interaction between tau oligomers, and is a Venus protein-based BiFC method in which the N-terminal and C-terminal non-fluorescent fragments of Venus protein are fused to tau. A further detailed definition and method for the tau-BiFC cell model are as described in Korean Patent No. 10-1546485.

Example 1: Analysis of Intracellular Tau Aggregation Inhibitory Activity

Figure 1:
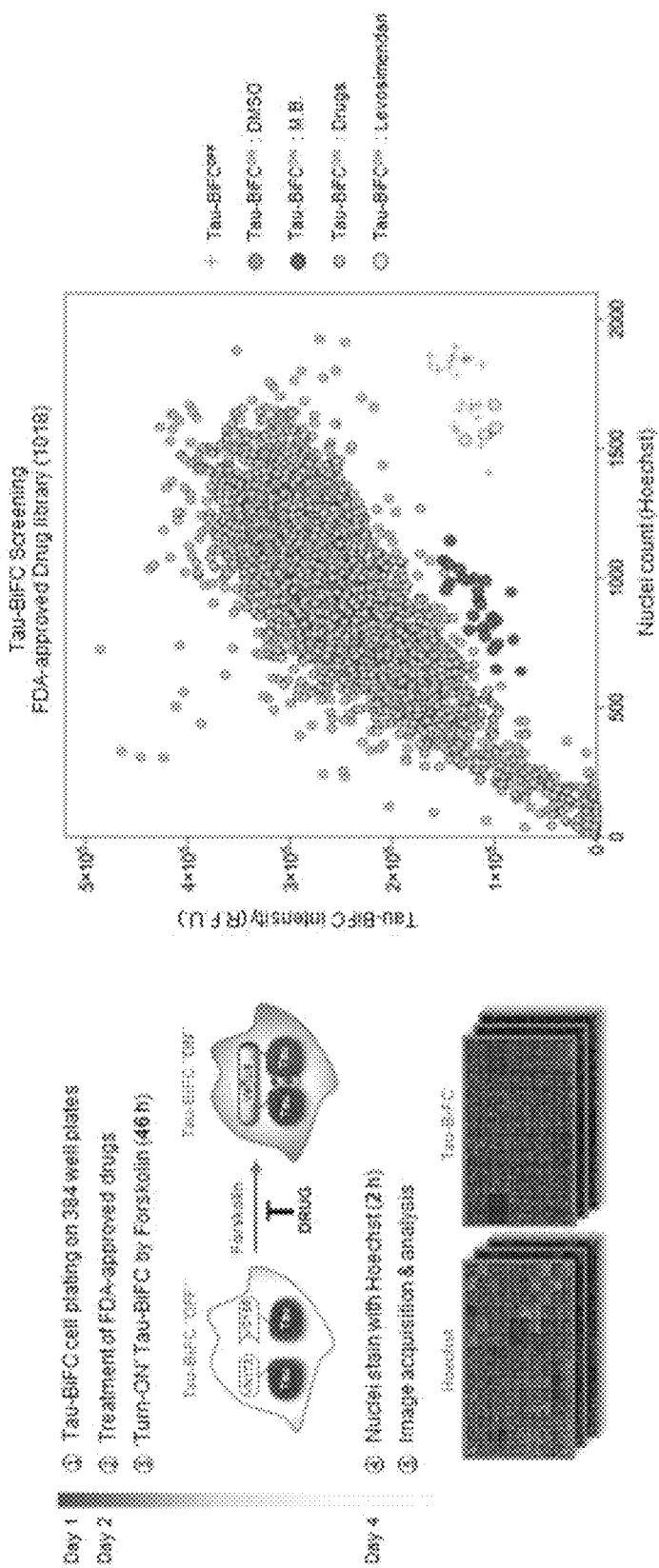
FIG. 1 shows the results of drug library screening according to an example of the present invention.

To screen a new tau aggregation inhibitor, tau-BiFC cell model making it possible to easily observe tau oligomer formation in living cells was treated an FDA-approved drug library (a total of 1018 compounds). As shown in a schematic view of FIG. 1, tau-BiFC cells were plated on a 384-well plate. On the next day, the tau-BiFC cells were treated with FDA-approved drugs (treatment concentration: 10 μM) together with the compound forskolin (treatment concentration: 30 μM) that activates tau kinase PKA to induce tau aggregation. After 46 hours, the tau aggregation inhibitory activities of the drugs were analyzed, and cell viability by the compounds was analyzed by cell nucleus staining with Hoechst. Among a total of 1018 compounds, the compound levosimendan was selected, which showed cell viability equal to that of drug-untreated normal cells (tau-BiFC$^{off}$) while showing a tau aggregation inhibitory activity equal to that of methylene blue (MB) known to show tau aggregation inhibitory activity (FIG. 1). To further confirm the tau aggregation inhibitory activity of the selected levosimendan, tau-BiFC cells were treated with DMSO, MB or levosimendan (treatment concentration: 10 μM) together with the compound forskolin (treatment concentration: 30 μM) that activates tau kinase PKA to induce tau aggregation. At this time, methylene blue (MB) known to show tau aggregation inhibitory activity was used as a comparative compound (positive control). After 48 hours, the tau aggregation inhibitory activity of the compound was analyzed, and cell viability by the compound was analyzed by cell nucleus staining with Hoechst.

Figure 2:
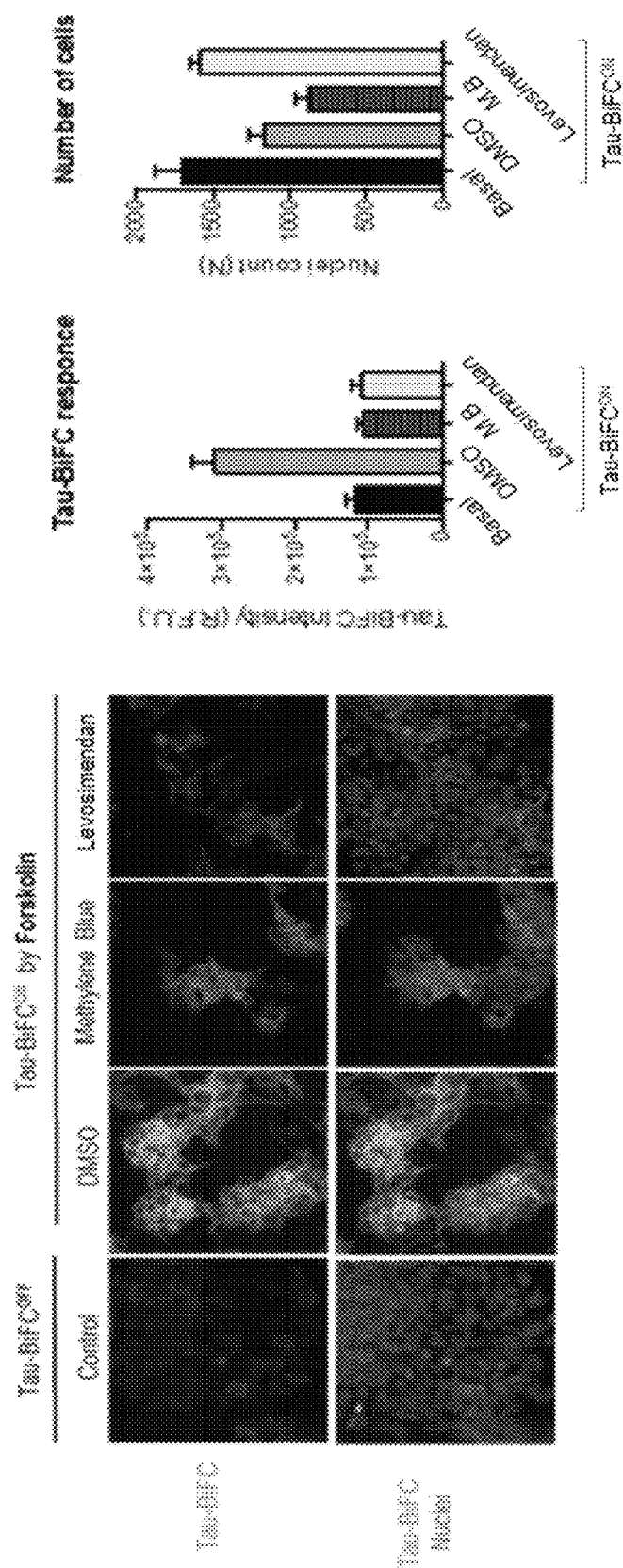
FIG. 2 shows the results of measuring the intracellular tau aggregation inhibitory activity and cytotoxicity of a levosimendan compound in an example of the present invention.

As a result, as can be seen in FIG. 2, in the state in which the tau-BiFC cell model worked (Tau-BiFC$^{ON}$), the fluorescence value (relative fluorescence units (RFU)) of the test group (levosimendan) decreased compared to that of the negative control group (DMSO). Furthermore, it could be seen that the fluorescence value of the test group (levosimendan) decreased, similar to that of the positive control group (MB). In addition, the number of nuclei stained with Hoechst was counted in order to evaluate cytotoxicity, and as a result, the number of the stained nuclei in the negative control group (DMSO) and the positive control group (MB) decreased, whereas the number of the stained nuclei in the test group (levosimendan) was similar to that in the normal control group (basal).

Accordingly, the compound levosimendan, which is less cytotoxic while showing intracellular tau aggregation activity similar to that of MB, was selected as a tau aggregation inhibitor.

In addition, in order to further confirm the tau aggregation inhibitory activity of the selected levosimendan compound in living cells, tau-BiFC cells were treated with the tau inducer forskolin (treatment concentration: 30 μM) together with 1, 3, 10, 30 or 100 μM of the levosimendan compound. After 48 hours, tau aggregation reactions in the cells were analyzed by analysis of tau-BiFC response, and cell viability was analyzed to determine the toxicity of the compound.

As a result, as shown in FIG. 3, the positive control group (MB) and the test group (levosimendan) showed a concentration-dependent decrease in the fluorescence value, and the $IC_{50}$ was 2.2 μM. The cells treated with the levosimendan compound (treatment concentration: 10 μM) showed tau aggregation inhibitory activity and cell viability, which are similar to those of untreated cells.

Example 2: Analysis of Tau Phosphorylation Inhibitory Activity

In order to confirm whether the levosimendan compound would show tau aggregation inhibitory activity by inhibiting tau phosphorylation, Tau-BiFC cells were treated with the tau aggregation inducer forskolin (treatment concentration: 30 μM) and the levosimendan compound (treatment concentration: 15 μM). After 36 hours, the tau-BiFC cell lysates were analyzed by Western blot analysis to measure tau phosphorylation.

As a result, as shown in FIG. 4, tau phosphorylation in the positive control group (+, MB) and the test group (+, levosimendan) decreased compared to that in the forskolin-treated cells (+). The test group (+, levosimendan) showed tau phosphorylation decreases of about 34% at tau phosphorylation Ser199 and about 35% at Ser396.

Example 3: Analysis of Neuronal Cell Protective Activity

Whether the levosimendan compound would protect neuronal cells from neuronal cell damage was examined. First, mouse cerebral cortical neuronal cells (E18, DIV8) were treated with the levosimendan compound (treatment concentration: 10 μM), and after 2 hours, the neuronal cells were treated with the tau protein TauK18P301L (treatment concentration: 20 μg/mL) that shows neuronal cell damage and intracellular tau aggregation.

Figure 5:
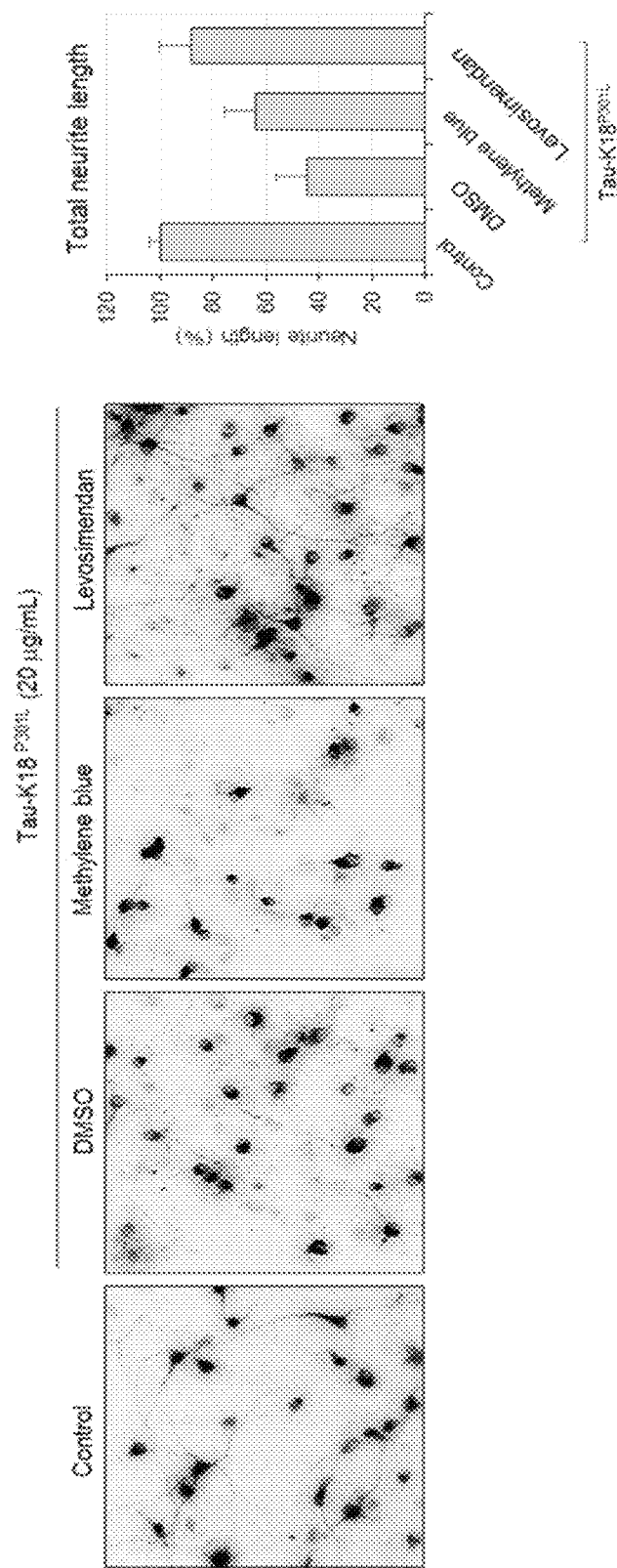
FIG. 5 shows the results of measuring the protective activity of a levosimendan compound against neuronal cell damage in an example of the present invention.

As a result, as shown in FIG. 5, damage to neuronal cells and neurite length in the test group (levosimendan) decreased compared to that in the negative control group (DMSO) and the positive control group (MB). However, the neuronal cell morphology and neurite length of the test group were similar to those of the control group. This suggests that the levosimendan compound has protective activity against neuronal cell damage caused by TauK18P301L.

Example 4: In Vitro Analysis of Tau Aggregation Inhibitory Activity of Levosimendan Compound The levosimendan compound showing tau aggregation inhibitory activity inhibited tau phosphorylation, but did not affect changes in tau kinase activity. Thus, whether the levosimendan compound would be involved in the tau aggregation process to inhibit tau aggregation was examined. Specifically, whether the levosimendan compound would inhibit the tau aggregation process was analyzed in vitro, and whether the levosimendan compound would prevent additional aggregation of aggregated tau and dissociate the aggregation was analyzed in vitro. The tau aggregation process (Tau pre-Agg+100 uM DTT+0.1 mg/mL Heparin, incubated at 37° C.) in vitro was treated with varying concentrations of the levosimendan compound, and the degree of tau aggregation was analyzed with ThS (Thioflavin S). The ThS is a dye capable of measuring tau aggregation in vitro in real time, and is used as a fluorescence probe that detects β-sheet aggregation.

Figure 6:
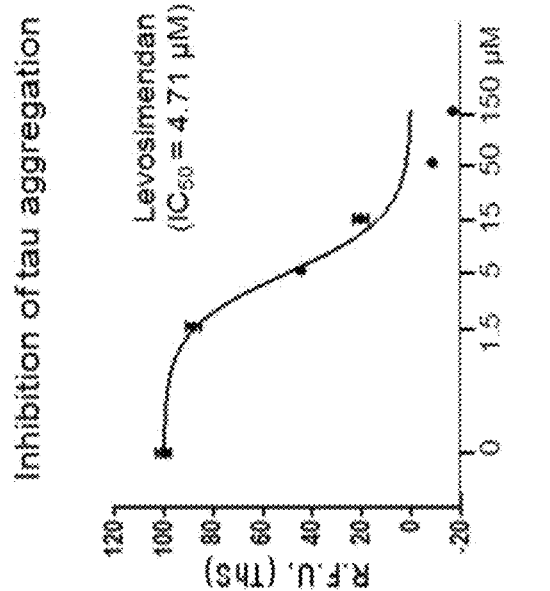
FIG. 6 shows the results of measuring the direct tau aggregation inhibitory activity of a levosimendan compound in vitro in an example of the present invention.
Figure 6:
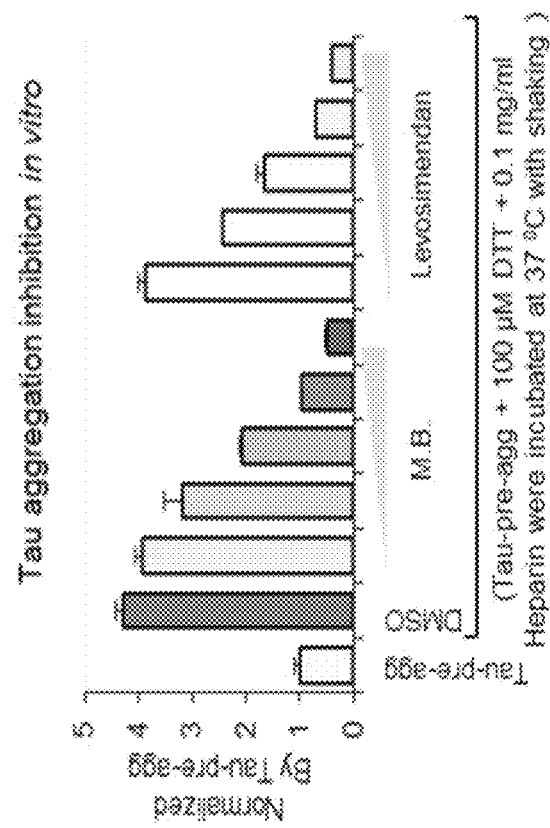

As a result, as graphically shown in FIG. 6, the levosimendan compound showed the effect of directly inhibiting tau aggregation in vitro. The $IC_{50}$ of the levosimendan compound in vitro was 4.71 μM.

Figure 7:
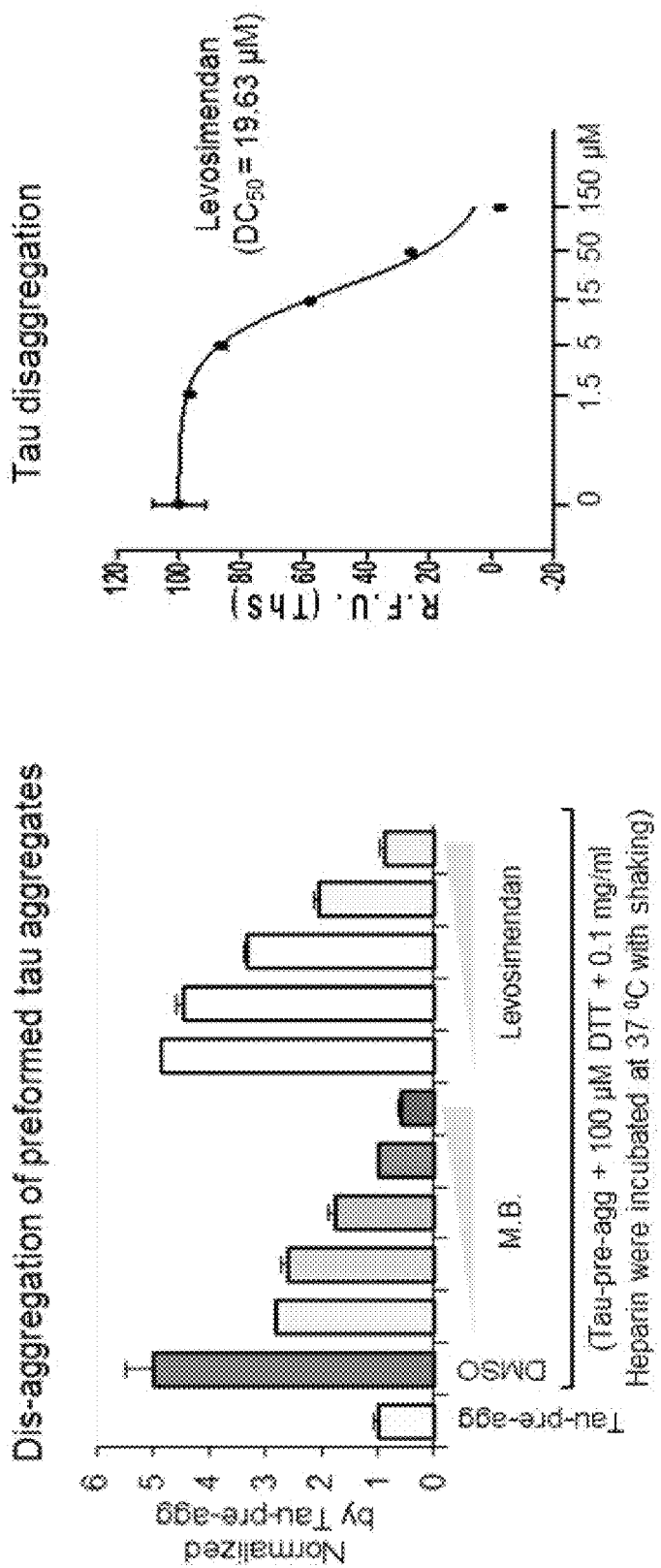
FIG. 7 shows the results of measuring the tau disaggregation ability of a levosimendan compound in vitro in an example of the present invention.

In addition, tau aggregates (Tau-Agg+100 uM DTT+0.1 mg/mL Heparin, incubated at 37° C.) in vitro were treated with varying concentrations of the levosimendan compound, and as a result, it was shown that the levosimendan compound had the effect of dissociating tau aggregates (FIG. 7).

Example 5: Analysis of Tau Aggregation Inhibitory Activity of Levosimendan Compound The levosimendan compound has two metabolite forms (activated (OR-1855) and activated (OR-1896)). The OR-1896 compound resulting from acetylation of the OR-1855 compound is known to remain in vivo for a long period of time to exhibit the drug effect. Thus, tau-BiFC cells were treated with each of the levosimendan compound and the two metabolites in order to examine whether any of these compounds would exhibit tau aggregation inhibitory activity. Specifically, tau-BiFC cells were treated with varying concentrations of each of MB, levosimendan, OR-1855 and OR-1896 compounds together with the tau aggregation inducer forskolin (treatment concentration: 30 μM). After 48 hours, the extent of tau aggregation in the cells was analyzed.

Figure 8:
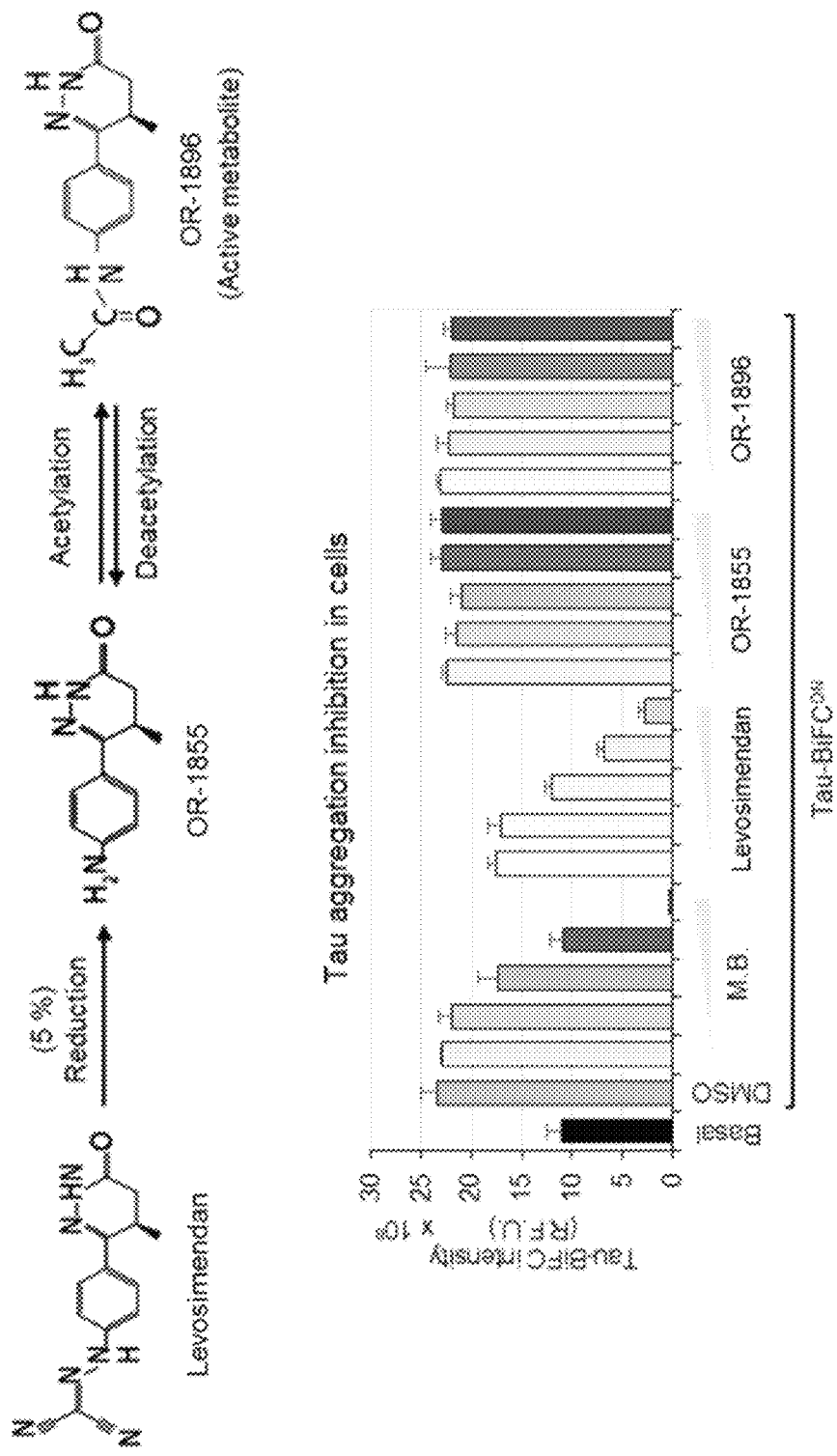
FIG. 8 shows the results of measuring the tau aggregation inhibitory activity of a levosimendan compound derivative in an example of the present invention.

As a result, as shown in FIG. 8, tau aggregation in the test group (levosimendan) decreased similar to that in the positive control group (MB). In other words, the levosimendan compound showed tau aggregation inhibitory activity in a concentration-dependent manner.

However, the OR-1855 and OR-1896 compounds did not show tau aggregation inhibitory activity. This indicates that the metabolite forms of levosimendan do not show tau aggregation inhibitory activity in cells.

As described above, according to the present invention, the levosimendan compound, an optically active isomer thereof, or a pharmaceutically acceptable salt thereof is effective in inhibiting tau aggregation and phosphorylation, and may be used for the prevention and/or treatment of neurodegenerative diseases and tau-related diseases.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A composition for treating tau aggregation-related diseases, comprising:
   a levosimendan compound or a pharmaceutically acceptable salt, stereoisomer or solvate thereof;
   at least one pharmaceutically acceptable carrier; and
   an active agent selected from the group consisting of an antioxidant, a cholinesterase inhibitor, and a combination thereof,
   wherein the levosimendan compound is represented by the following formula 1:
   Formula 1

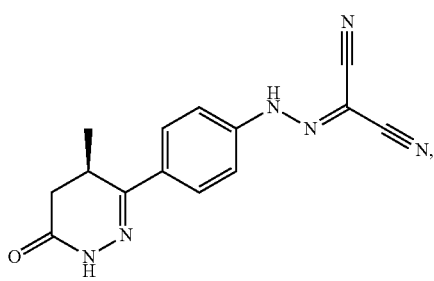 [SMILES: C[C@@H]1CC(=O)NN=C1c1ccc(NN=C(C#N)C#N)cc1]

and
   wherein the tau aggregation-related diseases are selected from the group consisting of Alzheimer disease, Parkinson's disease, tauopathy.

2. The composition of claim 1, wherein the tauopathy is selected from the group consisting of progressive supranuclear palsy, corticobasal degeneration, argyrophilic grain disease, peak disease, and inherited frontotemporal dementia.

3. A health functional food for treating tau aggregation-related diseases, comprising:
   a levosimendan compound or a pharmaceutically acceptable salt, stereoisomer or solvate thereof,
   wherein the levosimendan compound is represented by the following formula 1:
   Formula 1

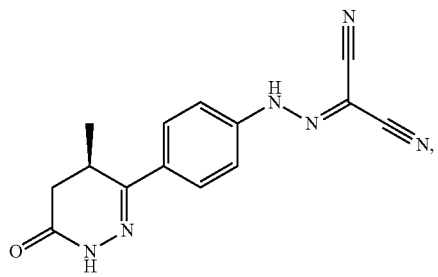 [SMILES: C[C@@H]1CC(=O)NN=C1c1ccc(NN=C(C#N)C#N)cc1]

and
   wherein the tau aggregation-related diseases are selected from the group consisting of Alzheimer disease, Parkinson's disease, and tauopathy.

* * * * *